United States Patent [19]
Carter

[11] Patent Number: 4,958,372
[45] Date of Patent: Sep. 18, 1990

[54] HEARING PROTECTOR UTILIZING AURAL REFLEX MECHANISM

[75] Inventor: Norman L. Carter, East Roseville, Australia

[73] Assignee: The Commonwealth of Australia, Phillip, Australia

[21] Appl. No.: 327,740

[22] Filed: Mar. 25, 1989

[30] Foreign Application Priority Data

Oct. 12, 1987 [AU] Australia ................................. PI4832

[51] Int. Cl.⁵ ............................................. A61F 11/02
[52] U.S. Cl. ....................................................... 381/72
[58] Field of Search ..................................... 381/72, 79

[56] References Cited

U.S. PATENT DOCUMENTS

| | | | |
|---|---|---|---|
| 3,271,520 | 9/1966 | Fletcher et al. | 381/72 |
| 4,181,818 | 1/1980 | Shenier | 381/72 |
| 4,677,678 | 6/1987 | McCutchen | 381/72 |

FOREIGN PATENT DOCUMENTS

| | | | |
|---|---|---|---|
| 1115455 | 4/1956 | France | 381/79 |
| 0108879 | 6/1983 | Japan | 381/79 |
| 2160075 | 12/1985 | United Kingdom | 381/79 |

OTHER PUBLICATIONS

Fletcher et al., "Protective Effect of the Acoustic Reflex for Impulsive Noises", Journal of the Acoustical Society of America, vol. 32, No. 3, Mar. 1960.

*Primary Examiner*—Forester W. Isen
*Attorney, Agent, or Firm*—Harness, Dickey & Pierce

[57] ABSTRACT

The effectiveness of electronic earmuffs is improved by incorporating a mechanism which causes the middle ear muscles to contract before an intense sound is generated. This contraction is achieved by incorporating a wireless receiver into the earmuff. Immediately prior to the generation of the intense sound, the wireless receiver receives a signal which causes it to generate a loud, non-damaging sound in a loudspeaker in the earmuff. The received signal is generated by a radio frequency transmitter that is activated immediately prior to the activation of the mechanism producing the intense sound. The non-damaging loud sound from the loudspeaker causes the middle ear muscles to contract (this is a natural reflex of the ear). The intense sound is received outside the earmuff before the reflex contraction of the middle ear muscles has been relaxed.

4 Claims, 1 Drawing Sheet

HEARING PROTECTOR UTILIZING AURAL REFLEX MECHANISM

TECHNICAL FIELD

This invention concerns hearing protection. More particularly, it concerns a method and apparatus for reducing the likelihood of hearing loss due to loud impulsive sounds.

BACKGROUND TO THE INVENTION

Traditionally, in loud noise environments, hearing has been protected by the use of earmuffs or ear plugs. In severe noise environments, the preferred practice has been to use both ear plugs and earmuffs to protect hearing. Workers in noisy environments, despite the danger to their hearing, have often objected to the use of earmuffs and ear plugs because of the sense of isolation that is often felt when such devices are used. Nevertheless, management has usually insisted on the use of earmuffs in noisy industrial environments, because a supervisor can readily check whether a worker in such an environment is using the protection, whereas it is not easy to determine whether a worker is using ear plugs.

This perceived problem with earmuffs and ear plugs was partly responsible for the development of the so-called "electronic earmuff", with which the sound incident upon an ear is controlled using an automatic gain control amplifier. This amplifier receives signals from a microphone and its output signal is used to activate a small loudspeaker mounted adjacent to the ear being protected. The gain of the amplifier is such that sound incident upon the microphone, up to a predetermined level, results in a sound level from the loudspeaker of approximately the same sound level. When the level of incident sound upon the microphone exceeds the predetermined level, the gain of the automatic gain control amplifier acts to suppress the level of sound generated by the loudspeaker to a non-hazardous level. This facility allows speech communication in quiet regions to take place easily but protects the user of the "electronic earmuff" from hazardous noise levels.

Unfortunately, even the electronic earmuff does not provide complete protection of the hearing of a wearer of the earmuff. Sound can "leak" past the earmuff through the natural groove between the jaw and the mastoid bone. Earmuffs can also be disturbed by sudden movements of the head and if they are accidentally knocked. The electronic earmuff has thus been regarded as able to provide only partially adequate protection against loud impulsive sounds—that is, sounds of high intensity which occur for short periods of time, such as the sound when an artillery shell is fired, or a drop forge or a metal press is activated.

One of the known physiological features of the human ear is the automatic contraction of small muscles in the middle ear, notably the stapedious muscle in response to very loud sounds. When such muscular contraction takes place, the transmission of sound from the ear drum through to the inner ear is attenuated. Since damage to hearing due to noise occurs in the inner ear, anything which reduces the sound energy reaching the inner ear acts as a hearing protector, to a certain degree. The contraction of the muscles in the middle ear attenuates the sound transmitted by about 14 dB at frequencies below about 2,000 Hz. Since the sound energy from artillery firing and the like peaks at about 1,000 Hz, this natural protection is potentially useful in environments subjected to impulsive noise.

Unfortunately, this reflex muscular contraction (a) takes from 100 to 200 milliseconds to become effective, and (b) "adapts" or "fatigues" quickly. Thus protection from the energy from brief intense sounds can only occur if the impulsive sounds are generated in rapid succession, and no protection is provided by this mechanism against the first impulsive sound or from continuous loud sounds.

Although this natural form of hearing protection has been known for many years, its potential for use in noisy environments has been reported only once—in 1962 in US tanks to protect the hearing of the crewmen of a tank when the tank gun was fired.

DISCLOSURE OF THE PRESENT INVENTION

It is an object of the present invention to utilise the known natural contraction of the muscles of the middle ear to provide enhanced protection of the hearing of persons using "electronic" earmuffs of the type described above.

This objective is achieved by generating, immediately before creating the impulsive noise, a loud but non-damaging sound in the audio frequency band from the loudspeaker of the electronic earmuff, to cause the middle ear muscles of a wearer of the earmuff to contract. This loud sound generation is achieved by a radio transmission of a signal immediately before the initiation of the impulsive sound, the transmitted signal being received by a receiver incorporated into the electronic earmuff. The output signal from this receiver is not fed into the automatic gain control amplifier, but separately activates the loudspeaker to generate the required loud but non-damaging sound. The middle ear muscles thus contract before the impulsive noise is heard, and provide the additional "natural" attenuation to the sound which penetrates the earmuff.

Thus, according to the present invention, a method of enhancing the protection of hearing in an environment where brief, intense sounds are produced comprises the steps of (a) supplying each person in the environment with an electronic earmuff having a protective shell adapted to surround the ear of a wearer of the earmuff, a microphone outside the protective shell, an automatic gain control system for controlling the level of signals from the microphone, the output of the automatic gain control system being input to a loudspeaker mounted within the protective shell; the electronic earmuff also including a wireless receiver having its output connected to said loudspeaker; and (b) transmitting, immediately before the production of a brief, intense sound, a radio frequency signal adapted to be received by said wireless receiver, said radio frequency signal being modulated so that, upon its receipt by said wireless receiver, the wireless receiver produces an output signal which causes said loudspeaker to generate a loud but non-damaging sound adjacent to the ear of said wearer of the earmuff; whereby the middle ear muscles of the wearer of the earmuff are contracted immediately prior to the reception, by said wearer, of the brief, intense sound.

Also according to the present invention, there is provided apparatus for providing enhanced protection of hearing in an environment where brief, intense sounds are produced, said apparatus comprising (i) a radio frequency transmission system associated with the generation of the sounds and (ii) an electronic earmuff; in which (a) the electronic earmuff comprises a protective shell adapted to surround the ear of a wearer of the earmuff, a microphone outside the protective shell, an automatic gain control system for controlling the level of signals from the microphone, the output of the automatic gain control system being input to a loudspeaker mounted within the protective shell; the electronic earmuff also including a wireless receiver having its output connected to said loudspeaker; and (b) the radio frequency transmission system comprises a firing signal generator which upon actuation generates a signal which operates a mechanism which produces a brief, intense sound; a delay line connected between the firing signal generator and said mechanism; a burst generator connected to said firing signal generator, said burst generator producing a signal which is transmitted by a radio frequency transmitter for reception by said wireless receiver.

Preferably the radio transmission and wireless receiver operate as an inductive field transmitter and receiver, since short range transmission is almost invariably involved.

An embodiment of the invention will now be described, with reference to the accompanying drawings.

DETAILED DESCRIPTION OF THE ILLUSTRATED EMBODIMENTS

Figure 1:
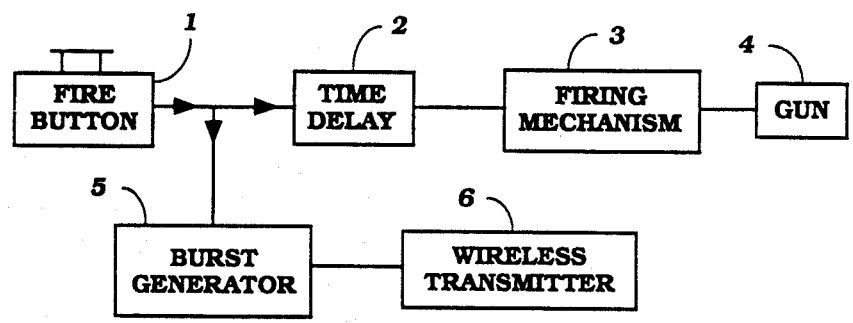
FIG. 1 is a block diagram illustrating the initiation system for a mechanism which produces impulsive noise, which includes features of the present invention.

The arrangement shown in FIG. 1 is a gun firing arrangement. It will be appreciated, however, that a gun has been used to illustrate one particular application of the present invention, namely, in an artillery range, and that the invention may be used in any impulsive noise generating system, several examples of which have been mentioned already in this specification. It will also be appreciated that although the term "firing signal generator" has been adopted in the statement of the apparatus form of the present invention above, and this term is especially apposite in gun firing, the term is intended to encompass the apparatus or unit (for example, a switch) which generates a signal that activates the mechanism that produces a brief, intensive sound (that is, an impulsive sound).

Referring now to FIG. 1, a gun 4 is fired by the actuation of the firing mechanism 3. The firing mechanism 3 is actuated by a signal from a fire button (a firing signal generator) 1. In the absence of the present invention, the output from the fire button 1 would be connected directly to the firing mechanism 3. The present invention, however, requires the output signal from the fire button to be connected also to a burst generator 5, and for the signal to the firing mechanism 3 to be delayed by a delay line 2.

When the burst generator 5 is activated by the signal from the fire button 1, it produces a burst of noise in the audio frequency band which is input to the radio transmitter 6. The delay line 2 delays the signal to firing mechanism 3 for a time—typically 150 to 200 milliseconds—sufficient to enable the noise signal to be transmitted by the transmitter 6 before the firing mechanism is actuated, and the gun 4 is fired.

Figure 2:
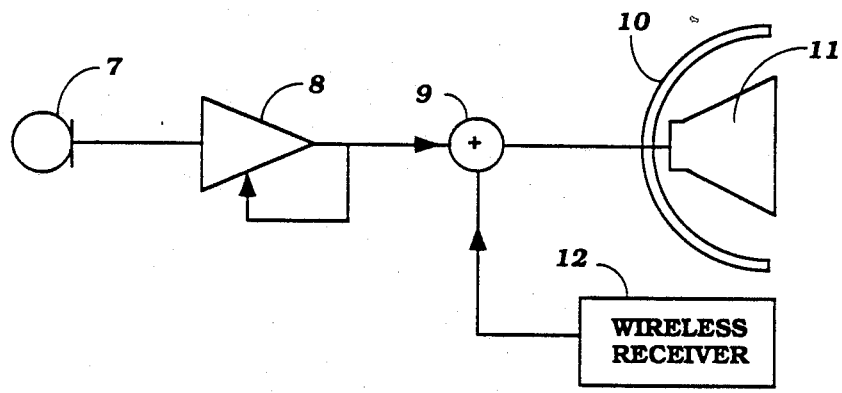
FIG. 2 is a block diagram illustrating an electronic earmuff incorporating the wireless receiver feature of the present invention.

Referring now to FIG. 2, the person skilled in the field of hearing protection will recognise the illustration of a conventional electronic earmuff comprising a microphone 7, an automatic gain control amplifier 8, an earmuff shell 10 and a small loudspeaker 11. In the normal use of the electronic earmuff, the shell 10 surrounds the exposed ear of a wearer of the muff to exclude normal ambient noise. Sounds incident upon the earmuff are detected by the microphone 7 and are converted into an electrical signal which is input into an automatic gain control amplifier 8. After amplitude modification by the amplifier 8, the electrical signal is passed through a summing point 9 (included as part of the present invention) and to the loudspeaker 11.

The automatic gain control (AGC) amplifier 8 is designed to ensure that when sound levels below hazard level are incident upon the earmuff, the signal to the loudspeaker 11 is such that the sound level presented to a wearer of the muff by the loudspeaker is similar to the sound level detected by the microphone 7. When the sound level at the microphone 7 becomes hazardous, the AGC amplifier reduces its gain so that hazardous sound levels are not presented to the ear by the loudspeaker 11. This arrangement allows speech communication to take place easily but protects the wearer of the electronic earmuff against hazardous noise levels.

Those skilled in this art will appreciate that the microphone and AGC system are normally an assembly on the shell 10, but have been drawn outside the shell in FIG. 2 for clarity.

The modification of the electronic earmuff required by the present invention is the inclusion of a wireless receiver 12 (also normally mounted on, or in association with, the shell 10), the output of which is also connected, via the summing junction 9, to the loudspeaker 11.

When the fire button (see FIG. 1) is pushed and the radio transmitter 6 transmits a burst of noise, this burst is picked up by the wireless receiver 12 and fed into the loudspeaker 11 via the summing junction 9. This action results in the generation of a loud—but not hazardous—burst of sound from the loudspeaker 11 which elicits the reflex contraction of muscles in the middle ear of the wearer of the earmuff, thus providing enhanced protection when the loud impulsive noise from the gun is heard.

Preferably the transmitter 6 and the receiver 12 are similar to those components used in the CALAID (trade mark) induction field communication systems, for those components have been optimally designed for short range wireless communication. However, other transmission/reception systems may be used, including optical (for example, infra-red), radio field or audio induction loop systems.

The various items of equipment illustrated in the drawings, such as the burst generator, the delay line and AGC system, are known forms of electronic apparatus, with which persons skilled in this art are familiar.

Incidentally, a delay of 150 to 200 milliseconds in the actuation of the firing mechanism of a gun should not affect the accuracy of gunners firing heavy artillery (especially when in training).

I claim:

1. A method of enhancing the protection of hearing in an environment where brief, intense sounds are produced, said method comprising the steps of (a) supplying each person in the environment with an electronic earmuff having (i) a protective shell adapted to surround the ear of a wearer of the earmuff, (ii) a microphone outside the protective shell, and (iii) an automatic gain control system for controlling the level of signals from the microphone, the output of the automatic gain control system being input to a loudspeaker mounted within the protective shell; the electronic earmuff also including a wireless receiver having its output connected to said loudspeaker; and (b) transmitting, immediately before the production of a brief, intense sound, a radio frequency signal that is received by said wireless receiver, said radio frequency signal being modulated so that, upon its receipt by said wireless receiver, the wireless receiver produces an output signal which causes said loudspeaker to generate a loud but non-damaging sound adjacent to the ear of said wearer of the earmuff;

whereby the middle ear muscles of the wearer of the earmuff are contracted immediately prior to the reception, by said wearer, of the brief, intense sound.

2. A method as defined in claim 1, in which the radio frequency signal comprises the signal from a radio transmitter, modulated by an input thereto of audio noise.

3. Apparatus for providing enhanced protection of hearing in an environment where brief, intense sounds are produced, said apparatus comprising a radio frequency transmission system associated with the generation of said intense sounds and an electronic earmuff; in which (a) the electronic earmuff comprises a protective shell adapted to surround the ear of a wearer of the earmuff, a microphone outside the protective shell, an automatic gain control system for controlling the level of signals from the microphone, the output of the automatic gain control system being input to a loudspeaker mounted within the protective shell; the electronic earmuff also including a wireless receiver having its output connected to said loudspeaker; and (b) the radio frequency transmission system comprises (i) a firing signal generator which upon actuation generates a signal which operates a mechanism which produces a brief, intense sound, (ii) a delay line connected between the firing signal generator and said mechanism, and (iii) a burst generator connected to said firing signal generator, said burst generator producing a signal which is transmitted by a radio frequency transmitter for reception by said wireless receiver.

4. Apparatus as defined in claim 3, in which the transmitter and the receiver comprise an induction field radio communication system.

* * * * *